United States Patent [19]

Durley, III

[11] 4,413,629

[45] Nov. 8, 1983

[54] PORTABLE ULTRASONIC DOPPLER SYSTEM

[75] Inventor: Benton A. Durley, III, Fox Lake, Ill.

[73] Assignee: Cryomedics, Inc., Bridgeport, Conn.

[21] Appl. No.: 370,858

[22] Filed: Apr. 22, 1982

[51] Int. Cl.³ ............................................. A61B 10/00
[52] U.S. Cl. ..................................... 128/660; 128/661
[58] Field of Search ............................... 128/660–661, 128/663; 73/597, 628, 861.25, 821.25

[56] References Cited

U.S. PATENT DOCUMENTS

| | | | |
|---|---|---|---|
| 3,972,320 | 8/1976 | Kalman | 128/706 |
| 4,086,916 | 5/1978 | Freeman et al. | 128/663 |
| 4,248,241 | 2/1981 | Tacchi | 128/715 X |

FOREIGN PATENT DOCUMENTS 1584347  2/1981  United Kingdom ............... 128/660

OTHER PUBLICATIONS

"Ultrasound Stethoscope" Medsonics Brochure, USCI, A Division of C.R. Band, Inc., P.O. Box 566 Concord Road Billerica, Massachusetts 01821.
Carter, J. "Blood Flow Measurement During Exercise in Sheep Using Doppler Ultrasonic Method," Med. & Biol. Engig & Computing 5/81 vol. 19, pp. 373–376.

Knutti, J. W. et al., "Integrated Circuit Implantable Systems" ISA Transactions vol. 19 #4 (1980 pp. 47–53).

Primary Examiner—Kyle L. Howell
Assistant Examiner—Francis J. Jaworski

[57] ABSTRACT

A portable ultrasonic Doppler System for sensing movement, e.g. fetal heartrate, within a body. A handheld unit includes a housing containing an ultrasonic transmitter and an ultrasonic receiver. The ultrasonic receiver detects ultrasonic energy emitted from the ultrasonic transmitter and reflected off of the moving object being monitored. The handheld unit also includes a radio frequency transmitter for transmitting a carrier modulated in accordance with the response of the ultrasonic receiver. A radio frequency receiver unit, separate from the handheld unit, receives the signal broadcast by the handheld unit. The receiver unit drives a speaker or earphone to provide an audio output for listening to the moving object being monitored. Digital display and memory circuitry is also provided which can be used in conjunction with said receiver unit to store and display data indicative of the movement being monitored. In conjunction with the handheld unit, a patient being monitored becomes the radio frequency antenna and the doctor becomes an extension of the antenna ground plane, providing a highly efficient radio link between the handheld unit and the receiver unit.

20 Claims, 12 Drawing Figures

PORTABLE ULTRASONIC DOPPLER SYSTEM

BACKGROUND OF THE INVENTION

The present invention relates generally to a portable ultrasonic Doppler system for sensing movement, and more specifically to such apparatus adapted for monitoring fetal heart rate.

The Doppler effect was first described in the 19th century by Austrian physicist Christian Doppler. In exlaining the Doppler effect, reference is often made to the pitch of the whistle of a moving train. When a train with its whistle blowing moves toward a stationary listener, the pitch of the whistle is higher than if the train were motionless. When the train moves away from the listener, the pitch of the whistle becomes lower. Ultrasonic Doppler probes used in fetal mointering operate by the same principal. Such a probe includes a transmitter crystal which emits an ultrasonic signal. The term "ultrasonic" means that the signal is higher in frequency than the highest sound that can be heard by the human ear, in other words, above 20,000 cycles per second. The Doppler probe is held against the mother's skin over the position of the fetal heart. The transmitter crystal sends its ultrasonic signal into the mother's body, and the signal is reflected back from the moving fetal heart to a receiving crystal in the Doppler probe. The movement of the fetal heart modifies the reflected frequency according to the heart velocity. This frequency shift is converted to an audible signal which is amplified so that it can be heard by a doctor. The ultrasonic Dopper technique is not limited to monitoring fetal heart rate. It is also useful, for example, in listening to the flow of blood through the arteries, as well as other movements within a living body. Such techniques can also be used to listen to other moving parts, e.g., in machines.

Electronic fetal monitoring is a routinely applied technique in the care of patients both prior to and during labor and delivery. Fetal heartbeats can be detected from the interior abdominal wall indirectly by means of a set of electrodes which pick up the weak fetal electrocardiogram on the maternal abdomen, a sensitive microphone which picks up fetal heart sounds, or an ultrasonic Doppler transducer which detects Doppler frequency shifts in ultrasonic energy reflected from moving components of the fetal cardiovascular system. Stethoscopes have also been used to listen to the fetal heartbeat.

The use of stethoscopes for listening to the fetal heartbeat has been unsatisfactory due to the high degree of extraneous or artifact noise which occurs during periods of labor contractions. Even prior to the commencement of labor, ordinary stethoscopes have been unsatisfactory because the sound of the fetal heart can be masked by the sound of the mother's heartbeat.

Ultrasonic Doppler systems for monitoring fetal heart rate are well known; however, those systems presently available are inconvenient to use. Most of the ultrasonic Doppler systems available to date include an ultrasound probe together with processing circuitry which is attached by wires to an earphone used by the physician. Other known systems utilize Doppler probes which are hard-wired to speakers which, for example, can be clipped to the physician's shirt pocket. An example of such a system is the model D100 Pocket Fetal Heart Detector sold by Sonicaid, Inc. of Fredericksburg, Va. The disadvantage to such systems is that the wires connecting the Doppler probe to the speaker or earphone can become tangled and get in the way during the physician's examination of the patient.

In order to overcome the inconvenience associated with hard-wired units, radiotelemetry systems have been proposed for clinical fetal monitoring. One such system is discussed in an article entitled "A Two-Channel Radiotelemetry System for Clinical Fetal Monitoring," by Michael R. Neuman and Edward O'Connor, BIOTELEMENTRY PATIENT MONITORING 7:104–121 (1980). In the system disclosed in this article, the fetal electrocardiogram is picked up by a scalp electrode and transmitted over a two-channel radio system to a separate receiver. The transmitter is packaged in a case and strapped to the patient's thigh. The system disclosed does not utilize an ultrasonic Doppler probe and, because its size requires it to be strapped to the patient, it is somewhat clumsy. Other known radiotelemetry systems for fetal monitoring are also bulky and therefore are inconvenient to use.

It would be advantageous to provide an ultrasonic Doppler system for monitoring movement, such as fetal heart rate, which is both portable and convenient to use. The separate components of such a system should not be interconnected by wires which can get in the way and become tangled. The Doppler probe should be easy to hold and adaptable to a variety of ultrasonic transducer configurations. It would be further advantageous for such a system to provide for both ultrasonic Doppler monitoring and conventional stethoscope-type direct sound monitoring. It would also be desirable to provide a means for recording the information sensed by such a system, and even to record the comments of a physician who is using the system.

The present invention relates to such a system.

SUMMARY OF THE INVENTION

In accordance with the present invention, a portable ultrasonic Doppler system is provided for sensing movement. The system comprises a handheld unit which includes a housing containing a transmitting element and a receiving element. Means are provided for energizing the transmitting element to emit ultrasonic energy. Means are also provided for detecting the response of the receiving element to ultrasonic energy emitted from the transmitting element and reflected to the receiving element by a remote object. Radio frequency transmitter means are provided for transmitting a radio frequency signal modulated in accordance with the response of the receiving element. The ultrasonic Doppler system also comprises a radio frequency receiver unit to receive the signal transmitted from the handheld unit. The radio frequency receiver includes audio output means for producing an audible signal in accordance with the response of the receiving element to the reflected ultrasonic energy.

As used herein, the term, "radio frequency" is intended to encompass any of the various signal transmission schemes that will be apparent to those skilled in the art. Accordingly, the term should not be construed to foreclose the use of signal transmission in the infrared frequency spectrum, or any other frequency range over which signals can be broadcast.

The radio frequency transmitter means included in the handheld unit of the present invention can include an antenna which, in operation, is placed into electrical contact with the skin of a patient being monitored. In this manner, the patient effectively becomes the antenna for the system, resulting in improved coupling between the radio frequency transmitter means and the receiver unit. Further, a ground plane for the antenna can be provided in the handheld unit with either an exposed conductive portion or a capacitively—coupled portion, such that a doctor, holding the unit, becomes an extension of the ground plane, thereby increasing the effectiveness thereof. The combination of the patient as the transmission antenna and the doctor as the antenna ground plane provides for a highly efficient radio link between the handheld unit and the receiver unit. In operation, the doctor and patient act as a type of dipole antenna.

It will be appreciated by those skilled in the art that the present apparatus is not limited to use in medical diagnosis. The system is equally applicable to any noninvasive testing requirement, including the dynamic monitoring of moving objects within machinery.

These and other features and advantages of the present invention will become more apparent with the following detailed description of the invention in conjunction with the drawings.

DETAILED DESCRIPTION OF THE INVENTION

The present invention is concerned with sensing movement, e.g. the heartbeat of a fetus, through the use of ultrasonic Doppler techniques. The invention provides a portable system having essentially two components. One component is a handheld unit used by the operator of the system (e.g., a physician). The handheld unit is placed against the outside surface of a body (e.g., a patient) in which a movement is to be sensed. The other component of the present system is a radio frequency receiver which receives and reproduces, in audible form, information transmitted by the handheld unit. The person holding the handheld unit and the object in which movement is to be detected function together as a dipole antenna to facilitate the transmission of information from the handheld unit to the receiver.

Figure 1:
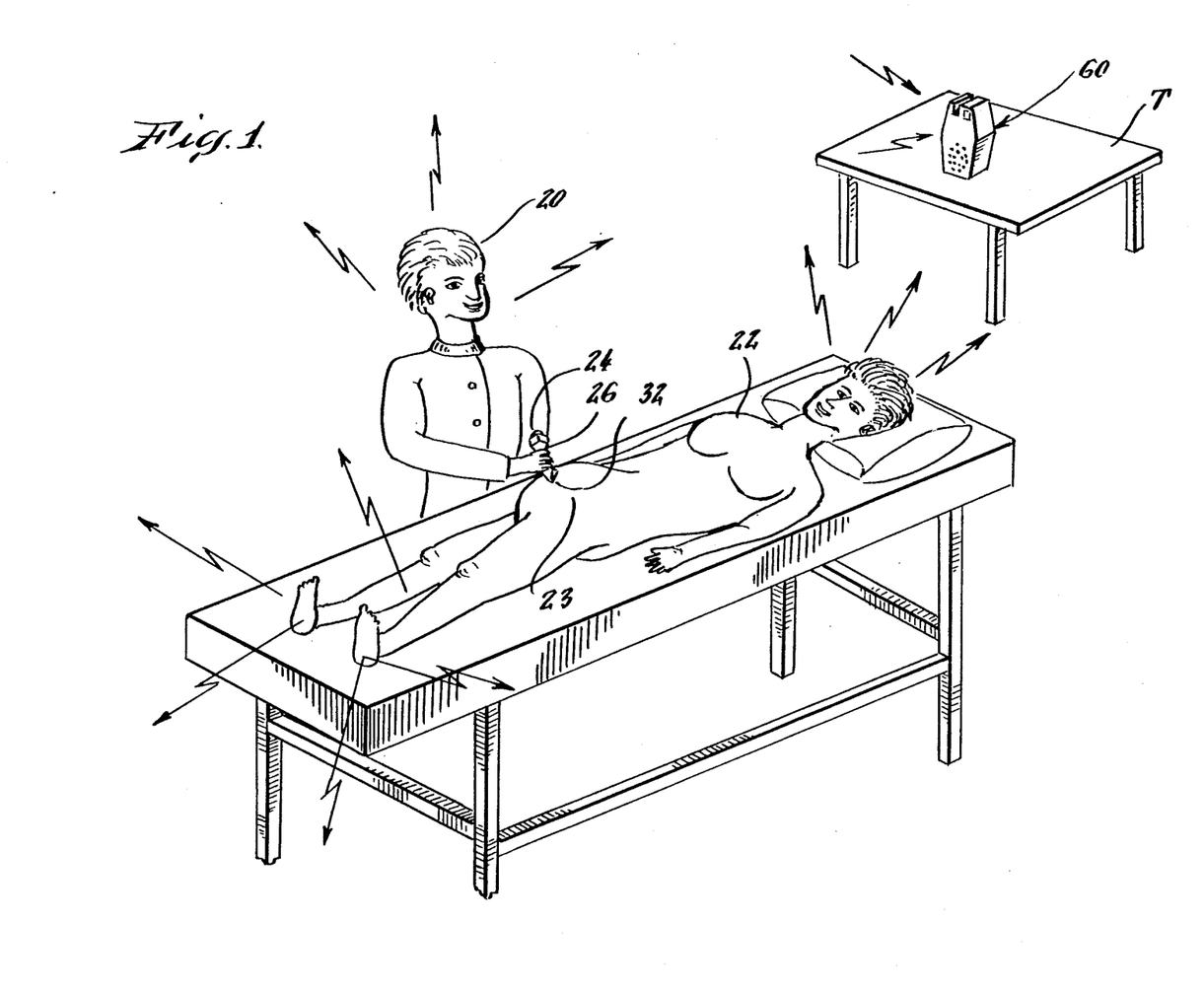
FIG. 1 is a sketch showing a physician using the present system for fetal monitoring.

FIG. 1 illustrates the use of the present system to monitor the heart rate of a fetus. A doctor 20 holds handheld unit 24 in his hand at handgrip portion 26. Head end 32 of handheld unit 24 is placed on the abdomen of a pregnant woman 22. In a manner to be explained hereinbelow, a radio frequency signal generated by handheld unit 24, and containing fetal heart rate information, is radiated from the doctor 20 and the pregnant woman 22. The radiated signal is detected by receiver unit 60, which produces an audible signal, through a speaker contained therein, in accordance with the received signal. Receiver unit 60 can also be supplied with an earphone jack so that doctor 20 can listen to the received signal privately, through an earphone.

Figure 2:
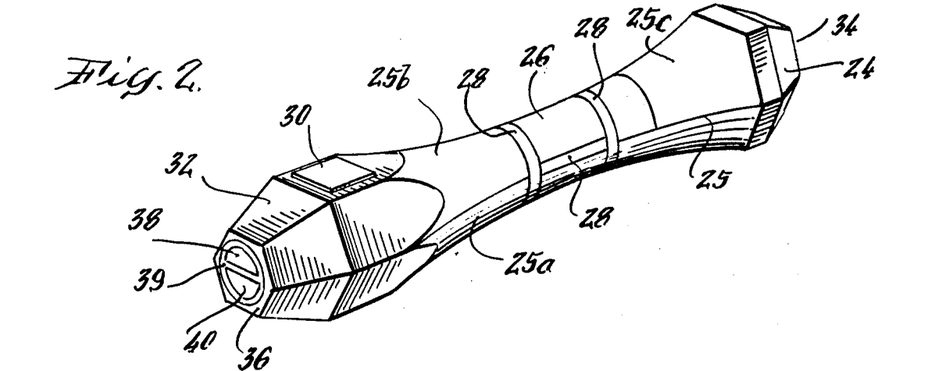
FIG. 2 is a perspective view of the handheld unit of the present invention.
Figure 3:
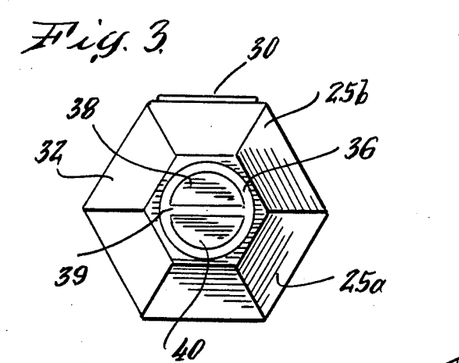
FIG. 3 is an end view of the handheld unit shown in FIG. 2.

Handheld unit 24 is shown in greater detail in FIGS. 2 through 6. As shown in FIG. 2, handheld unit 24 includes a head end 32 and a tail end 34. Button 30 is provided to actuate the switch which turns the internal circuitry of handheld unit 24 on and off. A handgrip portion 26 is provided on handheld unit 24 to provide a convenient way for a user to hold handheld unit 24. Within handgrip portion 26 is an electrically conductive zone 28 which will make either direct, conductive electrical contact with the hand of a person holding handheld unit 24, or indirect, capacitive contact with the hand of a person holding handheld unit 24. Conductive zone 28 can encompass up to 99% of handheld unit 24. Conductive zone 28 is coupled to circuitry internal to handheld unit 24.

Handheld unit 24 contains various electronic circuits, including an ultrasonic transmitter, an ultrasonic receiver, and a radio frequency transmitter. The ultrasonic transmitter circuit energizes a piezoelectric crystal 38 (see FIGS. 3-6) to emit ultrasonic energy. The ultrasonic receiver circuit detects the response of another piezoelectric crystal 40 to ultrasonic energy emitted by crystal 38 and reflected back to crystal 40 by a moving object 21 which, as shown in FIG. 5, the system is being used to monitor.

Figure 6:
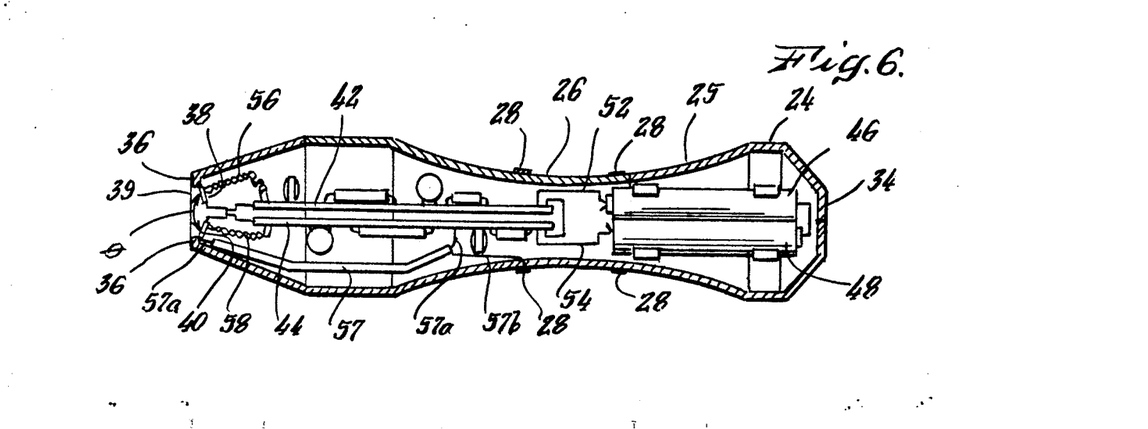
FIG. 6 is a cross-sectional view of the handheld unit shown in FIG. 2.

Handheld unit 24 comprises a three-piece housing which includes body portion 25a, cover portion 25b, and battery cover portion 25c. Housing components 25a, 25b, 25c, can be formed from any suitable material, such as plastic. The housing is generally cylindrical in shape; however, it has a hexagonal cross-section at its ends so that when handheld unit 24 is placed on a flat surface, it will not roll. The length of handheld unit 24 is preferably about eight inches long so that it can be easily balanced in the hand.

Ultrasonic transmit and receive crystals 38 and 40 are bonded to a preformed polyester body 39. Polyester body 39 is configured so that crystals 38 and 40 will be situated with an oblique angle $\phi$ therebetween. The angle $\phi$ is chosen to give a sufficient penetration of ultrasonic energy into a body and to provide proper reception of ultrasonic energy reflected back from the moving object being monitored.

Figure 5:
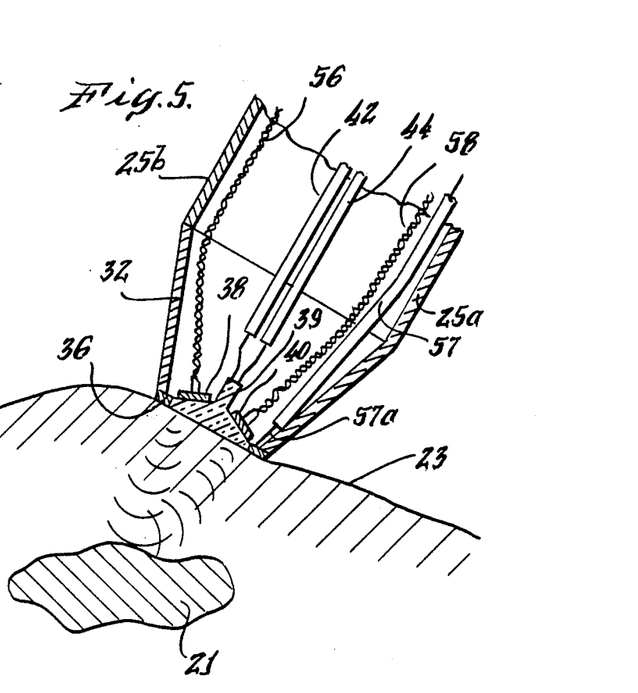
FIG. 5 is an enlarged cross-sectional view of the transducer end of the handheld unit, showing ultrasonic energy being emitted therefrom and reflected back from a moving object.

The operation of the ultrasonic Doppler portion of the present apparatus is shown in FIG. 5 which is a detailed drawing of head end 32 of handheld unit 24. In FIG. 5, head end 32 is shown placed on the skin 23 of a patient. A moving object 21 inside the patient's body is being sensed by the ultrasonic Doppler system. Ultrasonic energy is emitted from transmit crystal 38. The energy reflects off of moving object 21, back toward head end 32, and impinges upon the surface of receiving crystal 40. It will be understood that the focus for the ultrasonic beam, which is determined by the angle $\phi$, is chosen to coincide approximately with the position of the body organ being monitored when head end 32 of hand held unit 24 is properly positioned against skin 23. Such proper focusing serves to maximize the intensity of the reflected signal, and to minimize interference from other movements of the patient's body.

Also shown in FIG. 5 is a metal antenna electrode 36 which conductively contacts the skin 23 of a patient being monitored. Electrode 36 can be made from any conductive metal, preferably stainless steel. Antenna electrode 36 is connected to the internal conductor 57a of a shielded antenna wire which carries a radio frequency signal from the radio frequency transmitter in handheld unit 24.

FIG. 6 is a cross-sectional view of handheld unit 24 showing the various components internal thereto. Printed circuit boards 42 and 44 contain the various components which form the ultrasonic transmitter circuit, ultrasonic receiver circuit, and the radio frequency transmitter. Transmitter crystal 38 and receiver crystal 40 are shown mounted in head end 32 along with antenna electrode 36. FIG. 6 also shows the connection of braided portion 57b of shielded antenna wire 57 to the metal member forming conductive zone 28 in hand grip portion 26 of handheld unit 24. Also shown are batteries 46 and 48 which power the electronic circuitry of handheld unit 24.

Figure 7:
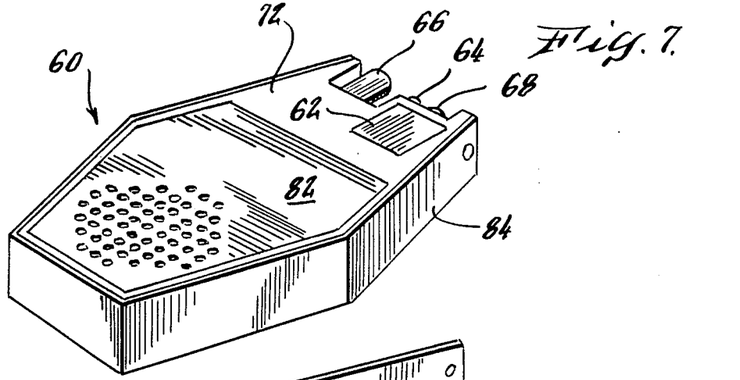
FIG. 7 is a perspective view of the receiver unit of the present invention.
Figure 8:
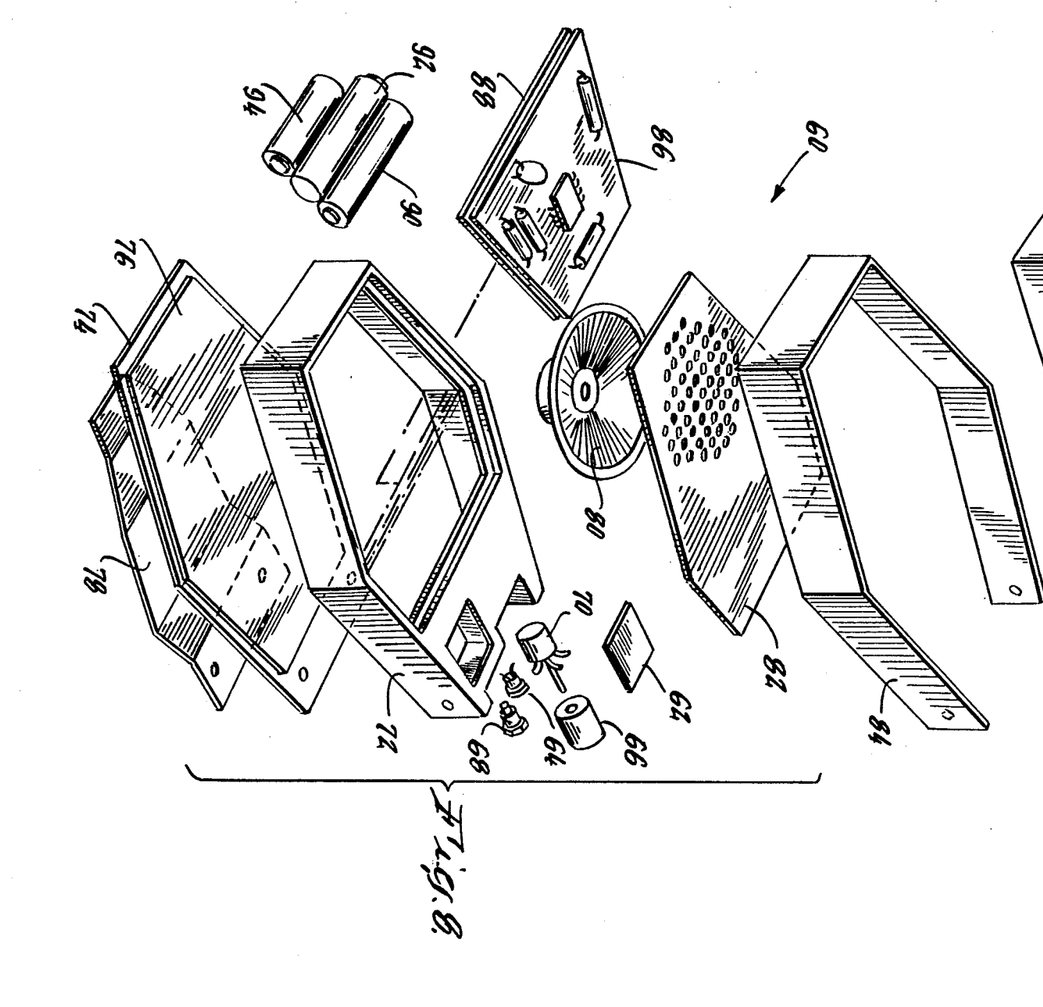
FIG. 8 is an exploded view of the receiver unit shown in FIG. 7.

The receiver unit of the present system is shown in FIGS. 7 and 8. Receiver unit 60 comprises a housing 72 which contains printed circuit boards 86 and 88. Circuit boards 86 and 88 contain the components which form the circuits that receive and process the radio frequency signal transmitted by handheld unit 24. A speaker 80 is provided within housing 72 for audibly reproducing the Doppler shift sounds detected by handheld unit 24. Perforated plate 82 enables the sound from speaker 80 to project from receiver unit 60. The back cover 74 of receiver unit 60 has a metal foil ground plane 76 attached thereto which, in conjunction with metal strip 84 forms a dipole antenna for the reception of the signal from handheld unit 24. Button 62 is provided in receiver unit 60 for turning the receiver circuitry on. A volume control 70 is adjustable by a system user by turning knob 66. Light emitting diode 64 indicates to the user that receiver unit 60 is turned on. Earphone jack 68 is provided so that the output of receiver unit 60 can be listened to on an earphone instead of through speaker 80. Batteries 90, 92, and 94 are used to power the receiver circuitry. The shape of housing 72 is such that receiver unit 60 can be slipped into the shirt pocket of a person using it. Clip 78 is provided so that receiver unit 60 may alternatively be clipped onto a belt, shirt pocket or the like.

The operation of the various electronic circuits used in conjunction with the present system will now be explained with reference to FIGS. 11 and 12.

Figure 11:
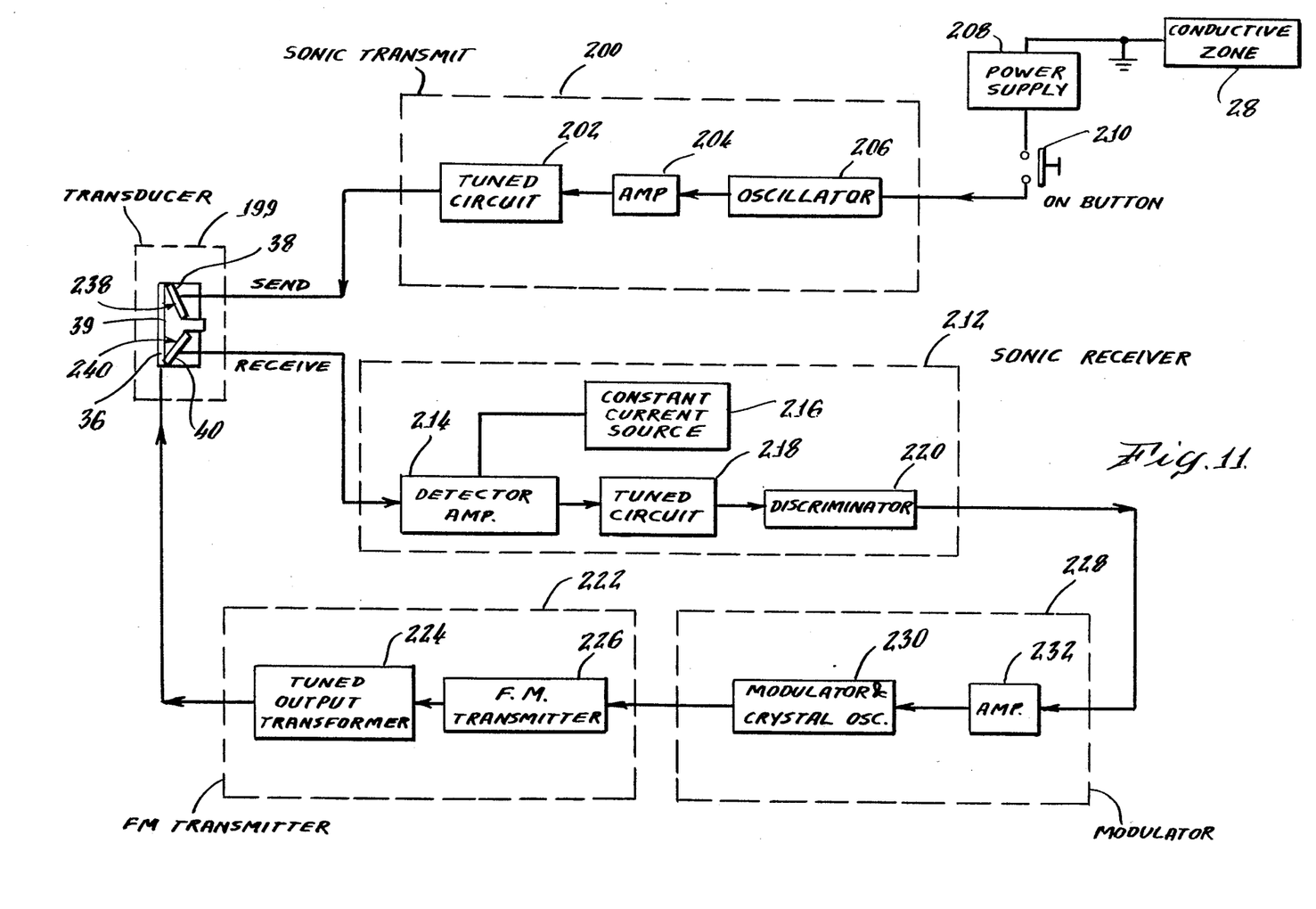
FIG. 11 is a block diagram of the sonic transmitter, sonic receiver and FM transmitter circuitry contained in the handheld unit of the present invention.

The circuits within handheld unit 24 are shown in FIG. 11. This circuitry is composed of 5 separate sections; namely, transducer 199, sonic transmitter 200, sonic receiver 212, modulator 228, and FM transmitter 222.

Transducer 199 comprises a rigid, non-conductive housing 39 with two piezoelectric crystals 38 and 40 bonded thereto at critical angles. Transducer 199 may comprise more than two piezoelectric crystals for certain applications, as will be described below in conjunction with FIG. 4. Non-conductive housing 39 also contains a conductive metal ring 36 around its periphery to provide electrical contact with the subject (e.g., patient) being monitored. Ring 36 serves as the FM transmitter antenna. Piezoelectric crystal 38 is a transmitter element which develops a mechanical vibration at a predetermined resonant ultrasonic frequency. The frequency is determined by the mechanical dimensions of crystal 38 as well as by the sonic transmit circuitry, generally designated by reference number 200. Transducer 199 is constructed to allow the vibrational motion produced by transmitter element 38 to be of sufficient amplitude to couple the ultrasonic energy emitted therefrom into the subject under observation, with little or no change in frequency or amplitude. Piezoelectric crystal 40 is a receiver element which has a receiving surface 240 disposed at an acute angle with respect to transmitting surface 238 of transmitter element 38. The angle between transmitter surface 238 and receiver surface 240 is critical as it determines the depth of possible reception by receiver element 40 of ultrasonic energy emitted from transmitter element 38. The wider the angle between surfaces 238 and 240, the greater will be the depth of possible reception. Sonic transmit circuit 200 contains an oscillator 206, an amplifier 204, and a tuned circuit 202. Oscillator 206 creates the proper frequency necessary to drive transmitter element 38 in a longitudinal (thickness) mode. Amplifier 204 develops the proper voltage level for driving tuned circuit 202 and piezoelectric transmitter element 38. Tuned circuit 202 consists of an inductor/capacitor network for providing the proper impedance match between amplifier 204 and transmitter element 38. In a preferred embodiment, the sonic transmit circuit 200 comprises integrated circuitry to provide for maximum stability and reliability.

Sonic receiver 212 contains a detector/amplifier 214, a constant current source 216, a tuned circuit 218, and a discriminator 220. Detector/amplifier 214 is coupled to receive an electrical signal from receiver element 40. The electrical signal is produced by the ultrasonic energy initially emitted by transmitter element 38 and reflected from the subject being examined back toward, and onto, receiver element 40. As already noted, receiver element 40 is a piezoelectric crystal which, upon excitation by the reflected ultrasonic energy, will produce a voltage. Detector amplifier 214 detects the electrical signal produced by receiver element 40 and amplifies it to a satisfactory voltage level for processing. The signal level is maintained through the use of constant current source 216, which ensures that the signal will be stable and of constant amplitude. Tuned circuit 218 selects the proper phase, frequency, and bandwidth for the detected signal while imparting a gain thereto. Discriminator 220 subtracts the high-frequency ultrasonic signal transmitted by transmitter element 38 to produce a difference signal representing the difference between the transmit frequency and the frequency shift which is caused by the velocity change of the object being observed. This shift is known as the "Doppler Shift" and the frequency difference caused thereby lies within the audio range (e.g., 20 to 20,000 cycles per second) and can be amplified by conventional audio amplifiers.

Modulator 228 comprises an audio amplifier 232 along with a modulator/crystal oscillator 230. Audio amplifier 232 amplifies the audio signal received from discriminator 220 of sonic receiver 212. The gain of this amplifier is moderately high. The output of amplifier 232 is coupled to the input of modulator/crystal oscillator 230. The modulator and crystal oscillator are designed to ensure a very stable frequency with the further capability of precisely varying this frequency over a narrow range. The crystal is selected to produce a constant frequency which is the center frequency or carrier of FM transmitter circuitry 222. The audio signal supplied by audio amplifier 232 to modulator/crystal oscillator 230 provides signal modulation for the FM carrier. Again, in a preferred embodiment, modulator 228 comprises integrated circuitry for simplicity and reliability.

FM transmitter subsystem 222 comprises an FM transmitter 226 and a tuned output transformer 224. FM transmitter 226 provides the proper voltage levels and impedance to drive tuned output transformer 224. Tuned output transformer 224 serves to impedance-match and maximize the output signal supplied to the radiating ring antenna 36 which is mounted around the periphery of transducer 199. The output impedance of tuned output transformer 224 is comparatively low so that signal amplitude will not change when handheld unit 24 is placed in contact with (such that it is electrically loaded by) the subject being examined. In this manner, the subject being examined becomes an extension of the radiating ring antenna. The result is that an RF-modulated signal is broadcast jointly by the radiating ring antenna 36 and the subject being examined.

Handheld unit 24 is equipped with a power supply 208 which, in a preferred embodiment, comprises longlife lithium batteries. Lithium batteries are selected because of their long shelf life and their energy density. A series switch 210 couples current from one potential of power supply 208 to all of the circuits within handheld unit 24. When switch 210 is closed, all of the handheld unit circuitry is energized. The other potential of power supply 208 is connected to the ground side of all circuit boards and to conductive zone 28.

Figure 12:
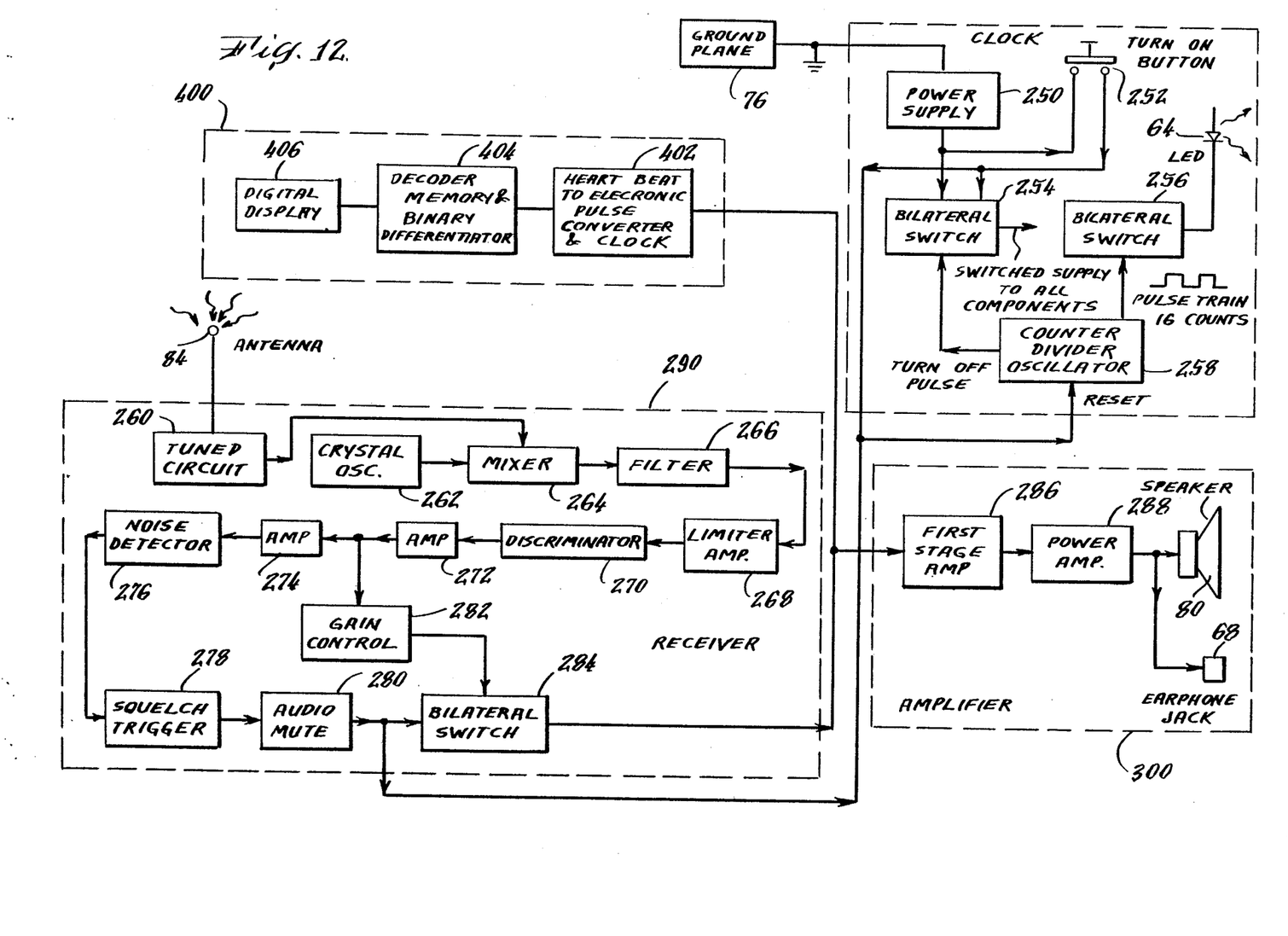
FIG. 12 is a block diagram of the circuitry contained in the receiver unit of the present invention, including an optional digital data storage and readout feature.

The circuitry within receiver unit 60 is shown in block diagram form in FIG. 12. Basically, this circuitry comprises a receiver section 290, a clock section 292, and an amplifier section 300.

Receiver section 290 consists of 13 subsections. These are a tuned circuit 260, a crystal oscillator 262, a mixer 264, filter circuitry 266, a limiter amplifer 268, a discrimintor 270, a first amplifier 272, a second amplifier 274, a noise detector 276, a squelch trigger 278, an audio mute circuit 280, a bilateral switch 284, and a gain control 282. The receiver antenna 84 is coupled to tuned circuit 260, and detects the RF-modulated signal broadcast by handheld unit 24. Tuned circuit 260 selects and transforms the low-amplitude signal from antenna 84 into a signal of greater amplitude at the desired tuned frequency. The enhanced signal from tuned circuit 260 is coupled into mixer 264. Crystal oscillator 262 provides a seperate frequency to mixer 264 which is slightly below the frequency of the signal transmitted by handheld unit 24 and detected by antenna 84.

Mixer 264 arithmetically subtracts the frequency from crystal oscillator 262 from the frequency detected by antenna 84 to provide a low-frequency signal. This low frequency signal is then input to filter 266 which removes any extraneous noise therefrom. The signal then passes from filter 266 through limiter amplifier 268 which conditions the signal by amplifying it and limiting its total voltage swing. From limiter amplifier 268, the signal is applied to discriminator 270 where it is demodulated to retrieve the audio signal which represents the Doppler shift, and hence the movement of the object monitored by handheld unit 24. The audio signal retreived by discriminator 270 is coupled to first amplifier 272 where it is amplified and fed to both second amplifer 274 and gain control 282. From gain control 282, the amplified signal is coupled to bilateral switch 284.

Bilateral switch 284 is basically an electronic relay or gate. This gate, when energized, passes the audio signal from gain control 282 to amplifier circuitry 300. The signal from second amplifier 274 is processed by noise detector 276 which is basically a high-pass filter, passing only frequencies above a predetermined level. Such high frequencies normally occur only when handheld unit 24 is not transmitting. Thus, the high frequencies can be used to provide an audio muting function. This is accomplished by passing the high frequencies from noise detector 276 to squelch trigger 278 which detects their presence and produces a trigger signal for audio mute circuit 280. Audio mute circuit 280 generates a zero-voltage or ground-potential output when the squelch- trigger signals are received. This ground potential de-energizes bilateral switch 284, causing its audio output to be grounded. As a result, a ground potential is supplied to the input of amplifier circuitry 300 when handheld unit 24 is not transmitting, muting the audio output of receiver unit 60. The output of audio mute circuit 280 is also coupled to clock circuitry 292 for a purpose to be described hereinbelow.

Amplifier circuitry 300 comprises first stage amplifer 286, power amplifier 288, speaker 80, and earphone jack 68. When handheld unit 24 is broadcasting an FM signal, the demodulated audio signal is received by first stage amplifer 286 from bilateral switch 284. First stage amplifier 286 amplifies the signal from bilateral switch 284 and inputs the amplified signal to power amplifier 288. Power amplifier 288 provides the proper current and voltage levels for driving speaker 80 or an earphone connected to earphone jack 68. Thus, an audible signal is produced which represents the velocity changes ("Doppler Shift") in the object being observed by handheld unit 24. If handheld unit 24 is de-activated the input to first stage amplifier 286 will be grounded due to the action of audio mute circuit 280 and bilateral switch 284 of receiver 290. In such an instance, no audible signal will be outputed from speaker 80 or an earphone connected to earphone jack 68.

Clock circuit 292 includes counter-divider/oscillator 258, bilaterial switch 254, bilateral switch 256, and power supply 250. Clock circuit 292 also includes a light emitting diode 64 and an on switch 252. As already noted, the output from audio mute circuit 280 of receiver section 290 is coupled to clock circuit 292 at the input of counter-divider/oscillator 258. Counter-divider/oscillator 258 serves as a clock for determining the length of time that the circuitry of FIG. 12 will operate after the handheld unit 24 has been deactivated. Counter-divider/oscillator 258 will be reset to zero anytime that handheld unit 24 is transmitting. If handheld unit 24 is deactivated, a pulse train of a predetermined number of counts commences. This pulse train is fed from counter-divider/oscillator 258 to bilateral switch 256 and permits bilateral switch 256 to switch light emitting diode 64 on and off for the duration of the predetermined count. Upon completion of said count, a signal is produced by counter-divider/oscillator 258 to de-energize bilateral switch 254. When bilateral switch 254 is de-energized, it switches one side of the potential voltage supplied by power supply 250 off, de-energizing all components within receiver unit 60. The other side of the potential voltage supplied by power supply 250 is connected to the ground side of all circuit boards and to metal foil ground plane 76. "On" switch 252 activates receiver section 290 and simultaneously resets counter-divider/oscillator 258 to zero. As in handheld unit 24, power supply 250 in receiver unit 60 can consist of long-lived batteries.

Additional circuitry can optionally be included in receiver unit 60 to provide a numerical readout and storage of the fetus' and/or the mother's heart rate(s) as well as the difference between the mother's heart rate and that of the fetus. The difference between the fetus' and mother's heart rates is indicative of the health and age of the fetus. Such additional circuitry can comprise three sections; namely, heart-beat-to-electronic-pulse converter and clock 402; decoder, memory, and binary differentiator 404; and digital display 406. The heart-beat-to-electronic-pulse converter and clock 402 counts the number of heart beats contained in a specific time interval determined by the clock and supplies a binary code to the decoder, memory, and binary differentiator circuit 404. This binary code contains three separate digits which are transmitted to either a "fetal" or "maternal" memory register within the decoder memory and binary differentiator 404, as determined by the unit's operator. In this manner, the maternal heart rate can be stored in one register, and that of the fetus in another register. The difference between the heart rates stored in these two registers is stored in a third register within the decoder memory and binary differentiator 404. The unit's operator has the option of selecting the maternal heart rate register, the fetal heart rate register, or the register indicating the difference between them. The data in the selected register can then be exhibited on the digital display 406.

Figure 4:
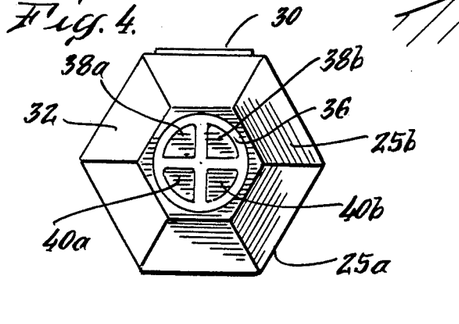
FIG. 4 is an end view of an alternate embodiment of the handheld unit shown in FIG. 2.
Figure 9:
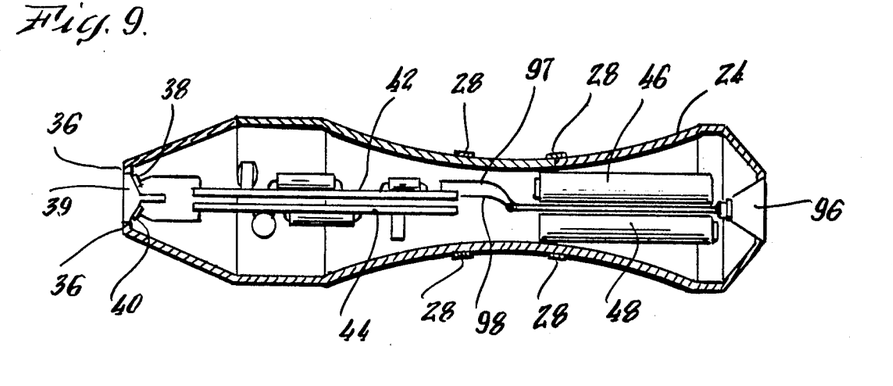
FIG. 9 is a cross-sectional view of an alternate embodiment of the handheld unit.
Figure 10:
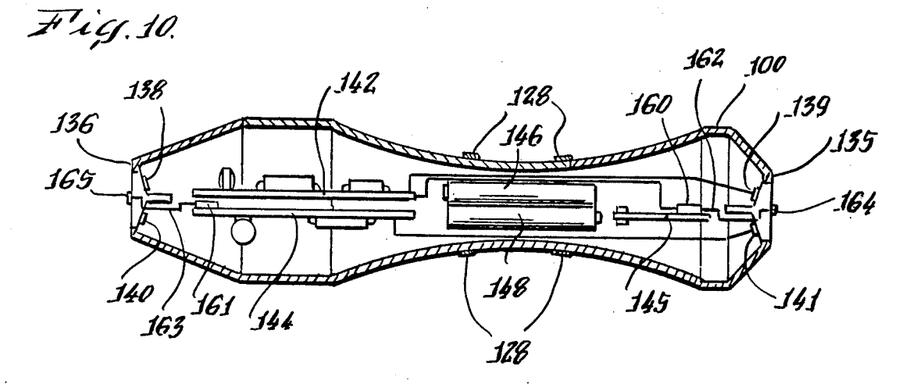
FIG. 10 is a cross-sectional view of yet another embodiment of a handheld unit in accordance with the present invention.

The present invention is adaptable to a variety of alternate embodiments, some of which are shown in FIGS. 4, 9, and 10. FIG. 4 is an end view of head end 32 of handheld unit 24. In the embodiment shown in FIG. 4, four piezoelectric crystals 38a, 38b, 40a, and 40b are used instead of only two such crystals. Piezoelectric crystals 38a, and 38b are transmitter elements, each adapted to transmit a different ultrasonic frequency. Piezoelectric crystals 40a and 40b are receiver elements adapted to receive the ultrasonic frequencies emitted from transmitter elements 38a and 38b respectively, after the transmitted ultrasonic energy has been reflected back from the moving object being monitored. By providing multiple frequency capabilities in this manner within head end 32, handheld unit 24 can be used to monitor a plurality of different objects. For example, transmitter element 38a and receiver element 40a could be adapted to monitor fetal heart rate, while transmitter element 38b and receiver element 40b can be adapted to monitor blood flow in the arterial and/or deep venous systems of the peripheral circulation. Those schooled in the art will appreciate that in order to achieve the different focusing parameters associated with different monitoring tasks, not only the frequency, but also the included angle between associated transmitter and receiver elements may have to be varied.

FIG. 9 shows an embodiment wherein a microphone 96 is mounted at the tail end 34 of handheld unit 24. Microphone 96 can be provided to enable the user of handheld unit 24 (e.g., a physician) to make comments which will be transmitted along with the audio portion of the modulated carrier broadcast by handheld unit 24, for permanent recording on a tape, or other means coupled to the audio output of receiver unit 60. In this manner, for example, a doctor listening to a fetal heart rate can make notes of pertinent factors which he needs to know during a subsequent playback of the recorded data. Alternatively, microphone 96 could be used to listen to a patient's heart beat in a conventional manner, in which case the present system would function as an electronic stethoscope.

In FIG. 10, a handheld unit 100 is shown having separate transducers symmetrically located at each end. One end includes a transmitter element 138 and a receiver element 140. These elements operate in conjunction with ring antenna 136 as already explained. The other end of handheld unit 100 includes transmitter element 139 and associated receiver element 141, along with a ring antenna 135. Both sets of transducers are coupled to the electronic circuitry on printed circuit boards 142 and 144. Conductive zone 128 is provided within the hand grip portion of handheld unit 100 so that a user of the device will, as explained above, function as the ground plane for the transmitting antenna. Batteries 146 and 148 are provided to power handheld unit 100. An additional feature shown in handheld unit 100 are switches 160 and 161, located at each end of handheld unit 100, to energize the circuitry therein whenever an end thereof is placed against the surface (e.g., skin) of a body to be monitored. One end of handheld unit 100 includes switch push button 165 which is coupled to switch 161 through actuator rod 163. When handheld unit 100 is appropriately placed on the surface of a body, push button 165 will be depressed, causing push rod 163 to actuate switch 161. Similarly, the other end of handheld unit 100 includes push button 164, push rod 162, and switch 160. Actuation of switch 161 will cause the circuitry associated with transmitter element 138 and receiver element 140 to be energized. Actuation of switch 160 will cause the circuitry associated with transmitter element 139 and receiver element 141 to be energized. When handheld unit 100 is not being used all circuitry will be de-energized.

As an additional feature, the handheld unit of the present invention can be placed into a sterile pouch (e.g., fabricated from rubber) for use of the handheld unit in an operating room. Operation of the apparatus is possible when the handheld unit is enclosed in the pouch since both the ultrasonic energy and the radio frequency energy will penetrate the pouch.

In addition to the various embodiments described herein for purposes of illustration, many variations and modifications could be made. It is intended to cover all of these variations and modifications which fall within the scope of the present invention, as recited in the following claims.

I claim:

1. A portable ultrasonic doppler system for sensing movement comprising:
 a handheld unit including a housing with a head end, a transmitting element mounted in said head end, means for energizing said transmitting element to emit ultrasonic energy, a receiving element mounted adjacent said transmitting element in said head end and responsive to ultrasonic energy emitted from said transmitting element and reflected to the receiving element by an object spaced therefrom, means for detecting the response of said receiving element to the reflected ultrasonic energy, radio-frequency transmitter means coupled to said detecting means for transmitting a radio-frequency signal modulated in accordance with the response of said receiving element, and an electrically conductive surface connected to the output of said radio-frequency transmitter means and situated externally of said handheld unit at said head end; and a radio-frequency receiver unit adapted to receive the radio-frequency signal transmitted from said handheld unit and including audio output means for producing an audible signal in accordance with the response of said receiving element;

said head end adapted to be placed on the body of a living being in which movement is to be sensed with said transmitting element positioned to emit ultrasonic energy toward a moving object within said body, said receiving element positioned to receive ultrasonic energy reflecting off of said moving object, and said electrically conductive surface in contact with said body, whereby said body serves as the antenna for transmitting said radio-frequency signal to said radio-frequency receiver unit.

2. The system of claim 1 wherein said transmitting element comprises a plurality of piezoelectric crystals, each adapted to emit a different ultrasonic frequency, and said receiving element comprises a plurality of piezoelectric crystals, each adapted to respond to one of the frequencies emitted by said transmitting element.

3. The system of claim 1 wherein said housing further comprises a hand grip portion.

4. The system of claim 3 further comprising an electrically conductive surface coupled at ground potential with respect to said radio-frequency transmitter means and situated externally of said handheld unit in said hand grip portion, whereby a person gripping said handheld unit in said hand grip portion serves as a ground plane for the transmission of said radio-frequency signal.

5. The system of claim 4 wherein said receiver unit is contained in a casing and includes first and second electrically conductive elements arranged within said casing to form a dipole antenna.

6. The system of claim 1 wherein said transmitting element comprises a piezoelectric crystal having a transmitting surface and said receiving element comprises a piezoelectric crystal having a receiving surface.

7. The system of claim 6 wherein the respective transmitting and receiving surfaces of said transmitting and receiving elements define an obtuse angle of less than 180° therebetween.

8. The system of claim 7 wherein said housing further comprises a hand grip portion.

9. The system of claim 8 further comprising an electrically conductive surface coupled at ground potential with respect to said radio-frequency transmitter means and situated externally of said handheld unit in said hand grip portion, whereby a person gripping said handheld unit in said hand grip portion serves as a ground plane for the transmission of said radio-frequency signal.

10. The system of claim 9 wherein said receiver unit is contained in a casing and includes first and second electrically conductive elements arranged within said casing to form a dipole antenna.

11. The system of claim 5 or 10 wherein said casing is adapted to fit in a shirt pocket.

12. The system of claim 1 or 9 wherein said handheld unit further includes a microphone mounted to said housing, and means coupling said microphone to said radio-frequency transmitter means for enabling said transmitter means to transmit a radio-frequency signal modulated in accordance with an output signal from said microphone.

13. The system of claim 12 wherein the audio output means of said receiver unit also produces an audible signal in accordance with the output signal from said microphone.

14. The system of claim 13 further comprising recording means coupled to said radio-frequency receiver unit for recording the response of said receiving element and the output signal from said microphone for future reference.

15. The system of claim 3 or 8 further comprising an electrically conductive surface coupled at ground potential with respect to said radio-frequency transmitter means and situated inside of said handheld unit in an area adjacent said hand grip portion, whereby a person gripping said handheld unit in said hand grip portion serves as a ground plane for the transmission of said radio-frequency signal.

16. The system of claim 1 further comprising display means operatively associated with said radio-frequency receiver unit for providing a visual display of data in accordance with the response of said receiving element.

17. The system of claim 16 further comprising memory means for storing data in accordance with the response of said receiving element, and means for coupling said memory means to said display means for selectively displaying said data.

18. A portable ultrasonic doppler system for sensing movement comprising:

a handheld unit including a housing, a plurality of transmitting elements mounted in said housing and each adapted to emit a different ultrasonic frequency, a plurality of receiving elements mounted in said housing and each adapted to respond to the frequency emitted by a different one of said transmitting elements and reflected to the receiving element by an object spaced therefrom, means for detecting the response of said receiving element to the reflected ultrasonic energy, and radio-frequency transmitter means coupled to said detecting means for transmitting a radio-frequency signal modulated in accordance with the response of said receiving elements; and a radio-frequency receiver unit adapted to receive the radio-frequency signal transmitted from said handheld unit and including audio output means for producing an audible signal in accordance with the response of said receiving element.

19. The system of claim 18 wherein said housing is generally cylindrical in shape and comprises a first end containing a first operatively associated transmitting and receiving element pair, and a second end containing a second operatively associated transmitting and receiving element pair.

20. The system of claim 19 further comprising first switch means at said first end for enabling said system to operate in conjunction with said first transmitting and receiving element pair when said first end is placed on the surface of a body in which movement is to be sensed, and second switch means at said second end for enabling said system to operate in conjunction with said second transmitting and receiving element pair when said second end is placed on the surface of a body in which movement is to be sensed.

* * * * *